US005710372A

United States Patent [19]
Becket

[11] Patent Number: 5,710,372
[45] Date of Patent: Jan. 20, 1998

[54] METHOD OF ANALYSIS FOR AQUEOUS FLUIDS

[75] Inventor: Giles J. P. Becket, Cincinnati, Ohio

[73] Assignee: Cincinnati Milacron Inc., Cincinnati, Ohio

[21] Appl. No.: 768,190

[22] Filed: Dec. 17, 1996

[51] Int. Cl.$^6$ .................. G01N 21/78; G01N 31/22; C09K 03/00

[52] U.S. Cl. .................. 73/53.01; 73/61.41; 73/61.71; 422/55; 436/167; 436/162

[58] Field of Search .................. 73/53.01, 61.54, 73/61.41, 61.71, 53.06, 61.52; 422/55, 56; 436/162, 167

[56] References Cited

U.S. PATENT DOCUMENTS

| | | | |
|---|---|---|---|
| 1,925,254 | 9/1933 | John | 73/53.06 |
| 3,215,498 | 11/1965 | Schlitt | 23/230 |
| 3,912,655 | 10/1975 | Shukla et al. | 252/408 |
| 3,914,174 | 10/1975 | Fuchs | 210/31 C |
| 3,963,421 | 6/1976 | Jones | 23/230 B |
| 4,059,407 | 11/1977 | Hochstrasser | 23/253 |
| 4,130,085 | 12/1978 | Hewitt | 118/315 |
| 4,752,587 | 6/1988 | Dickakian | 436/60 |
| 4,839,296 | 6/1989 | Kennedy et al. | 436/170 |
| 4,855,239 | 8/1989 | Rupe | 436/106 |
| 4,904,605 | 2/1990 | O'Brien et al. | 436/109 |
| 4,956,146 | 9/1990 | Yuhki et al. | 422/56 |
| 4,968,604 | 11/1990 | Beatty | 435/7 |
| 5,041,225 | 8/1991 | Norman | 210/500.36 |
| 5,071,623 | 12/1991 | Akutsu | 422/56 |
| 5,124,128 | 6/1992 | Hildenbrand et al. | 422/56 |
| 5,183,742 | 2/1993 | Omoto et al. | 435/14 |
| 5,229,299 | 7/1993 | Terry | 436/125 |
| 5,300,564 | 4/1994 | Avnir et al. | 525/54.1 |
| 5,310,525 | 5/1994 | Churchouse et al. | 422/56 |
| 5,312,591 | 5/1994 | Doi | 422/56 |
| 5,330,715 | 7/1994 | Blake et al. | 422/56 |
| 5,360,595 | 11/1994 | Bell et al. | 422/56 |
| 5,439,828 | 8/1995 | Masilamani et al. | 436/74 |
| 5,443,990 | 8/1995 | Harako | 436/74 |

FOREIGN PATENT DOCUMENTS

| | | | |
|---|---|---|---|
| 0023631 | 2/1981 | European Pat. Off. | G01N 33/50 |
| 9425856 | 11/1994 | WIPO | G01N 21/78 |

OTHER PUBLICATIONS

European Patents Abstracts, p. 121, week 9247, BEHW, B04, 92-383495/47, EP 513564 A2 –EP(A)_N.
Euopean Patents Report, p. 302, week 9002, EP(A)–N, BOEF, B04, 90–009699/02, EP-349934-A.

Primary Examiner—Hezron E. Williams
Assistant Examiner—J. David Wiggins
Attorney, Agent, or Firm—John W. Gregg; Donald Dunn

[57] ABSTRACT

A simple, convenient method is provided for measuring the concentration of a constituent of an aqueous fluid composition (e.g. aqueous machining fluid composition) and for measuring total alkalinity thereof. The method comprises the steps of a) contacting a solid state test device with the aqueous fluid wherein the solid state test device comprises a plurality of individual spaced apart test regions on an inert support, each test region comprising an inert matrix impregnated with a reagent selectively interactive with the constituent and a color indicator that produces a change in color in response to changes in the test region resulting from interaction between the reagent and the constituent and wherein the amount of reagent in each test region differs in a predetermined manner from the amount of reagent in adjacent test regions, and b) comparing the solid state test device after contact with the aqueous fluid to a constituent concentration color calibration scale for the same reagent, color indicator and constituent.

20 Claims, 1 Drawing Sheet

METHOD OF ANALYSIS FOR AQUEOUS FLUIDS

FIELD OF INVENTION

This invention is related to methods for measuring the concentration of a constituent of an aqueous fluid composition. More particularly this invention pertains to methods employing a color changing solid state measuring device for measuring the concentration of a constituent of an aqueous fluid.

BACKGROUND

Aqueous fluid compositions are employed in a variety of tasks and environments wherein a knowledge of the concentration of the various constituents of, as well as contaminants in, the fluid is important to insuring the proper and effective functioning and utilization of the fluid. Such aqueous fluid compositions for example are employed in cooling water tower systems, washing operations, machining processes, swimming pools, hydraulic fluids and plating operations. Thus methods and devices for the simple direct determination of constituent concentration, including contaminants, is important in the industrial arts. The detection of and determination of concentration of particular materials in aqueous based "body fluids" by simple and direct means is also important in the medical arts, an example of which is urine testing.

In the industrial arts, aqueous based machining fluids are employed and significantly contribute to the quality of machined objects and the productivity of machining operations or processes as well as in prolonging the life of the tools employed in the production of the machined objects. To obtain the maximum effectiveness and utilization of aqueous machining fluids it is important to determine and monitor the concentration of various constituents of the fluid. As used herein, the term "aqueous machining fluid" shall mean a complex aqueous liquid applied to the interface between a tool and a workpiece during the shaping of the workpiece by physical means. The physical means are principally mechanical means and are exemplified by grinding, machining, turning, rolling, punching, extruding, spinning, drawing and ironing, pressing and drilling operation.

Aqueous based machining fluids are typically used in recirculating systems in which fluid from a reservoir is supplied for application to the vicinity of contact between the tool and workpiece and is returned therefrom to the reservoir. With use and reuse of the metalworking liquid there occurs chemical and/or physical breakdown and/or physical loss of one or more constituents of the liquid during storage and use of aqueous machining fluids changes may occur which are adverse to effectiveness of the fluid: for example, decomposition of components induced by heat; oxidation resulting from contact with air; reaction with metal chips contaminating the fluid; microbial or fungicidal induced changes; evaporation of water; and, plating out of constituents individually and collectively. Loss of the functional constituents of aqueous based machining fluids (i.e. liquids) impair the effectiveness of the fluid for performing one or more specific functions, e.g. lubrication, emulsification, corrosion control, and control of microbial growth. Thus to control and maintain aqueous machining fluid effectiveness it is desirable to monitor the concentration of the constituents.

To combat the negative affects of changes in the composition of the aqueous based metalworking liquid occurring during storage and use, it is desirable to monitor the physical and/or chemical conditions of the fluid on a frequent basis. Such monitoring not only provides indications of changes, but also points to corrective measures to be taken to restore the effectiveness of the liquid and extend its useful life. Among the chemical and physical characteristics typically measured in such monitoring of the liquid are pH, dissolved oxygen, temperature, conductivity, microbial activity, surfactant or emulsifier activity, oil contamination, metal chip contamination and total alkalinity. Instrumental and wet analytical techniques are applied in the art to the measurement of these and other characteristics (e.g. concentration changes) of aqueous machining fluids. These techniques may be used on samples taken from a reservoir of the fluid being used in machining operations, particularly a reservoir that supplies the fluid to a number of machine tools for shaping workpieces (e.g. metal), commonly referred to as a "central system". The samples are commonly taken to a laboratory or other convenient location where the analyses and measurements are performed. Often the measurements are made at locations near or adjacent to the reservoir of metalworking fluid, particularly the outlet side of a central system reservoir feeding and machine tools. Some measurements (e.g. temperature, conductivity, pH and dissolved oxygen) are made of sensors placed in the flow path of the aqueous metalworking fluid being supplied to the metalworking machine tools. In such cases the measurement may be made on a continuous or intermittent bases.

The prior art manual or automated systems for determining the concentration of constituents of aqueous machining fluids are unsuitable for many machining operations. This is especially true in machining operations employing aqueous machining fluid reservoirs at individual machine tools and where there may be employed more than one low volume usage aqueous machining fluid formulation (e.g. separate aqueous machining fluid formulations for different machining operations). It is therefore desirable and advantageous to have a simple, easy to use, relatively convenient, low cost test method for rapid measurement of the concentration of a constituent of an aqueous machining fluid at the site of fluid utilization.

Solid state test devices, particularly simple to use solid state test devices based on analytical chemistry principles, have been employed in the art of fluid testing and significant progress has been made in recent times in providing more than a gross indication of both the presence of and concentration of a constituent (i.e. analyte) of an aqueous fluid. Such devices have relied upon the degree of color change for providing a measure of the concentration of the analyte. These solid state test devices have taken a number of forms one of which is known as a test strip. Such test strip typically consists of a substrate having a pad placed thereon wherein the pad has a paper matrix impregnated with a reagent reactive with the analyte. In prior art methods, this pad is contacted with or immersed in an aqueous fluid containing the analyte whose concentration or presence is to be determined. A color change is produced in the pad and the degree of color change in the pad is usually compared to a color comparison chart or may be read with an instrument such as a reflectance photometer to determine the analyte concentration. Most suitable for use at the site of the fluid are those test strips which may be read without use of instrumentation.

Various reagents have been employed in the art for making solid state test devices (e.g. test strips) usable in methods for determining the presence of and concentration of various constituents of aqueous based fluids. Generally, specific reagents are employed for determining the presence of and concentration of particular constituents of aqueous based fluids. Examples of such reagents and tests include sodium dichromate for measuring chlorides, melamine for measuring cyanuric, acid, nitroprusside for measuring ketones in urine, immunoglobulin for antibody assay, glucose oxidase/peroxidase/oxidizable indicator mixture for determining glucose in a body fluid and 2-methyl-5-nitroaniline, sodium nitrite, 2,4-dichloroabniline and 2,6-dichlorobenzene for bilirubin in urine. Thus it is seen that single compounds, mixtures of compounds, inorganic compounds, organic compounds and biological agents have been employed as reagents in solid state test devices such as test strips.

It is known in the art of solid state test devices to provide and use correction pads to correct for pH, coloring agents in the test fluid, interfering contaminants or constituents in the test fluid and interfering properties of the paper matrix used to hold the reagent in the pad. Test strip solid sate devices having multiple pads for simultaneously testing for different constituents in the same aqueous fluid and methods employing such test strips are known in the art. Along with these features, however, it is common in the part to provide non-instrumental test strip solid state test devices having a pad whose degree of color change resulting from contact with the test fluid is the basis for determining the concentration of the fluid constituent producing the change. Thus in prior art non-instrumental test methods using such test strips there are employed the steps of contacting such a test strip with an aqueous test fluid, producing a color change on the test pad whose degree of color change is proportional to the concentration in the test fluid of the constituent producing the color change and comparing the color change on the pad to a color calibration scale indicative of concentrations of the constituent producing the color change. The evaluation of color change, typically by comparison with a color chart or scale, requires discrimination of degree, shade or intensity of color. This method has the inherent disadvantages associated with visual discrimination of minor changes in degree, shade, or intensity of color, hence, making the methods highly subjective.

Known non-instrumental methods for determining the concentration of a constituent of an aqueous test fluid while being convenient, simple and easy to use, have inaccuracies attendant with the subjective character of the method. In particular, a) reproducibility of colors essential to the method, b) inaccuracies attendant with reading small changes in color for very dark or intense colors and c) the inaccuracies or gaps in the color calibration chart especially where the degree of color change would not be a linear function of the constituent concentration. It thus would be highly desirable to have a test strip method for measuring constituent concentration of an aqueous fluid that is accurate, minimizes subjectivity and would not depend upon the use of an instrument while being easy to use, simple and convenient.

SUMMARY OF INVENTION

This invention overcomes many of the disadvantages of prior art solid state device visual reading methods for measuring the concentration of a constituent of an aqueous based fluid composition (i.e. an aqueous fluid composition having at least one chemical constituent or component other than water) by reducing or eliminating the subjectivity of the visual readings associated with prior art methods.

It is an object of this invention to provide a simple convenient and easy to use method of measuring the concentration of a chemical constituent of an aqueous fluid composition by means of a solid state test device which provides a visually unambiguous indication of concentration.

A still further object of this invention is to provide a solid state test device method for measuring the concentration of a chemical constituent of an aqueous based machining fluid composition which provides a visually unambiguous indication of concentration.

It has been discovered that the foregoing objects and others, as will be apparent in the following description, examples and claims can be achieved by this invention for a method for measuring the concentration of a constituent of an aqueous fluid composition comprising the steps of a) contacting an aqueous fluid composition with a solid state test device comprising 1) an inert substrate and 2) a plurality of individual test regions spatially arranged on the substrate with each test region comprising an inert matrix impregnated with a reagent selectively interactive with the aqueous fluid constituents and a color indicator responsive to change in the test region resulting from the interaction between the reagent and the aqueous fluid constituent and wherein the amount of reagent impregnated in each test region differs from the amount in adjacent test regions in a predetermined manner, and b) comparing the solid state test device contacted by the aqueous fluid composition with a constituent concentration color calibration scale.

In accordance with one embodiment of this invention there is provided a method for measuring the concentration of a constituent of an aqueous machining fluid composition comprising the steps of a) contacting with the aqueous machining fluid composition a solid state test device comprising an inert support and a plurality of individual spaced apart test regions on said support, comprising an inert matrix impregnated with a reagent interactive with the constituent and a color indicator that undergoes a change in color in response to the changes in the test region resulting from interaction between the reagent and the constituent and wherein the amount of the reagent in each test region differs in a predetermined manner from the amount in adjacent test regions and b) comparing the solid state test device after contact with the aqueous machining fluid to a constituent concentration color calibration scale.

In a further embodiment of this invention there is provided a method for measuring the concentration of a constituent of an aqueous metalworking fluid composition comprising the steps of a) contacting with the metalworking fluid a solid state test device comprising an inert support and a plurality of individual spaced apart test regions on said support, comprising an "inert matrix impregnated with a reagent interactive with the constituent" and a color indicator that produces a change in color in response to the changes in the test region resulting from interaction of the reagent and the constituent and wherein the amount of reagent in each test region differs in a predetermined manner from the amount in adjacent test regions, and the constituent concentration is such that in response to direct contact of the solid state test device with the aqueous metalworking fluid a color change is produced in at least one test region, but not all the test regions, of the solid state test device and b) comparing the solid state test device after contact with the metalworking fluid to a constituent concentration color calibration scale.

In a still further embodiment of this invention there is provided a method for determining the total concentration of alkaline constituents in an aqueous machining fluid composition comprising the steps of a) contacting with the aqueous machining fluid a test strip solid state test device comprising an inert support strip and a plurality of individual spaced apart test pads, on said support, comprising an inert matrix impregnated with an "organic acid interactive with the alkaline constituents" and a pH color indicator, and wherein the amount of organic acid in each test pad differs in a predetermined manner from the amount of organic acid in adjacent best pads and b) comparing the test strip after contact with the aqueous machining fluid to an alkaline constituent concentration color calibration scale.

Other embodiments of this invention are contemplated wherein the aqueous fluid composition is an aqueous cleaning fluid composition, an aqueous plating bath composition, aqueous cooling fluid composition, aqueous based hydraulic fluid, aqueous processing fluids, aqueous etching fluids, aqueous quenching fluids, aqueous agricultural fluids and aqueous grinding fluids.

As the method of this invention does not require instrumentation for determination of concentration, it is particularly suitable for field use and on site measurement for determining and monitoring the condition of aqueous fluids. Such utilization of this invention can be helpful in 1) the industrial arts for monitoring and adjusting aqueous process fluids and providing a quality control over aqueous process and product fluids, 2) the control of aqueous fluid compositions for use in cooling systems, swimming pools and machining processes and 3) assessing the condition of water systems such as, for example, lakes, rivers and streams as well as industrial and commercial aqueous effluents or discharges.

BRIEF DESCRIPTION OF THE DRAWINGS

In the appended drawings

FIG. 4b is a top view of a test strip bearing a legend derived from the constituent concentration color calibration scale of FIG. 4a.

DETAILED DESCRIPTION OF INVENTION

It has been found that the disadvantages of the subjective evaluation of the degree of color change produced (i.e. assessing the degree of color change) in a test pad of a test strip solid state test device in prior art methods for measuring the concentration of a constituent of an aqueous based fluid composition can be minimized or overcome by the method of this invention. The concentration of a constituent of an aqueous fluid composition measured in accordance with the method of this invention comprises the steps of a) contacting with the aqueous fluid composition a solid state test device comprising 1) an inert support and 2) a plurality of individual test regions spatially arranged on the support, each test region comprising an inert matrix impregnated with a reagent selectively interactive with the aqueous fluid constituent and a color indicator wherein the amount of reagent in each test region differs in a predetermined manner from the amount of reagent in adjacent test regions so that a visually unambiguous pattern of color results in the test regions from interaction between the constituent and reagent, and b) comparing the solid state test device contacted by the aqueous fluid composition to a constituent concentration color calibration scale prepared for the reagent, the color indicator and the aqueous fluid constituent.

As used in this disclosure, the examples herein and the appended claims the term "support" shall mean a continuous solid member, preferably non-porous for carrying the test regions; the term "inert" shall mean resistant to chemical and physical degradation upon contact with the aqueous fluid composition and constituents thereof, the reagent and the color indicator; and the term "reagent," shall mean a substance that is interactive with the constituent whose concentration is being measured.

Figure 1:
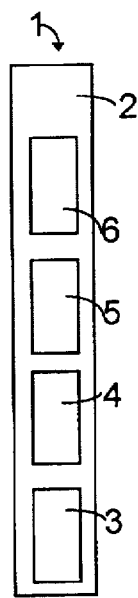
FIG. 1 is a top view of a test strip embodiment of the solid state test device of the method of this invention showing a substrate and a plurality of test pads thereon.
Figure 2:
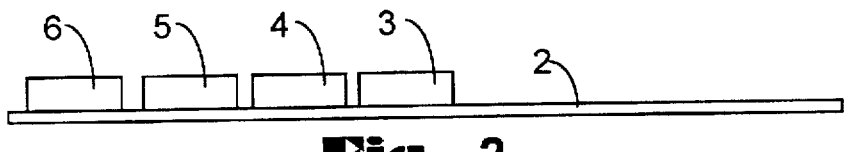
FIG. 2 is a side view of the test strip shown in FIG. 1 for purposes of showing the isolation of the test pads from each other.

This invention overcomes many if not all the disadvantages of visually subjective determination of color change and hence the disadvantages of use of color change to determine concentration of a constituent of an aqueous fluid. In contrast to prior art methods, the method of this invention employs a solid state test device as in FIG. 1 having a plurality of test regions (pads) 3, 4, 5 and 6 that are spaced along the inert support 2 of the device 1 in isolation from each other as shown in FIG. 2. Each of these test regions 3, 4, 5 and 6 (e.g. pads on a test strip) has an inert matrix impregnated with a color indicator and a reagent selectively interactive with the constituent whose concentration is being measured. The color indicator is chosen to produce a visually unambiguous change of color in response to interaction between the aqueous fluid constituent and the reagent. In accordance with this invention the amount of reagent in each of test regions 3, 4, 5 and 6 differs from the amount in the other test regions in a predetermined manner. The presence or absence of changes of color in the test regions, coupled with the predetermined difference in amount of reagent in each test region provides a visual display indicative of the concentration of the aqueous fluid constituent.

Figure 3:
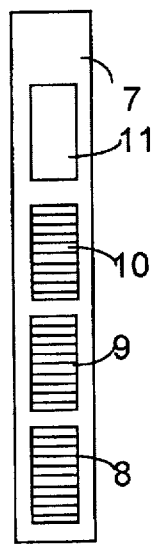
FIG. 3 is a top view of an exposed test strip solid state test device.

In the method of this invention the solid state test device 1 would be contacted by the aqueous fluid (e.g. by immersion). Such contact may for example produce a blue color in test pads 3, 4, and 5, but not in test pad 6 as represented by the lining of test regions shown in FIG. 3. By comparison of this exposed test strip 2 to a constituent concentration color calibration scale 12, shown in FIG. 4a, the constituent concentration can be determined by matching the color pattern of the test strip to the color patterns of the concentration calibration scale. From the concentration scale of FIG. 4a, it is known that the test strip as illustrated by FIG. 3 reflects a constituent concentration of 3%, i.e. there has been, a change of color of test pads 8, 9, and 10 (corresponding to test pads 3, 4, and 5 of FIG. 1) producing the pattern of change of color illustrated by column 15 of the color calibration scale 12. Thus in accordance with this invention there is removed the subjectivity of assessing a degree of color change and hence there is removed the disadvantages of such subjective assessment of a degree of color change.

Solid State Test Device

The solid state test device usable in the practice of this invention may take on a variety of forms and constructions. In one form there is provided a test strip solid state test device having an inert thin non-porous plastic strip support upon which is spatially disposed a plurality of individual test regions each separated from each other. The plastic strip support may be rigid or flexible. A test strip solid state test device usable in this invention is shown in FIGS. 1 and 2 wherein the test strip 1 has a thin rectangular support 2 which is made of a non-porous plastic, such as for example a polyolefin (e.g. polypropylene), upon which is attached four test areas 3 to 6 along the length of the strip with each test area or pad separated from the adjacent test area. Test areas 3 to 6 each have a matrix (e.g. filter paper) impregnated with a reagent (e.g. an organic acid) and an indicator (e.g. bromophenol blue) that undergoes a change in color when there is present sufficient constituent (i.e. alkaline constituent) the concentration of which is to be measured, that as a result of interaction (e.g. reaction) with the reagent in the pad (e.g. acid), a condition (e.g. pH) is achieved within the test region which induces the color indicator to undergo a change of color. The amount of reagent in the test pads 3 to 6 differs in a predetermined manner from pad to pad, increasing as you go from pad 3 to pad 6. Thus pad 4 has a larger amount of reagent than pad 3, pad 5 has a larger amount of reagent than pad 4 and pad 6 has a larger amount of reagent than pad 5. Each test pad 3, 4, 5 and 6 could contain the same amount of the color indicator.

In the method of this invention it is required that the amount of reagent in the test region be known and differs in a known and predetermined manner from one test region to the next test region in the plurality of test regions of the solid state test device. Thus, for example, in the solid state test device 1 of FIG. 1 the amount of reagent in test regions 3, 4, 5 and 6 may increase by a factor of 2 from test region 3 to test region 4, from test region 4 to test region 5 and from test region 5 to test region 6. Thus there might be an amount of reagent of 0.08 grams in the test pad 3, 0.16 grams of reagent in the test pad 4, 0.32 grams of reagent in the test pad 5 and 0.64 grams of reagent in the fourth test pad 6. Conversely the amount of reagent in test regions 3 to 6 may decrease by a factor of ½ from test region 3 to test region 4, from test region 4 to test region 5 and from test region 5 to test region 6. In the event it is desired to determine constituent concentrations over a range of values with a predetermined resolution, the amount of reagent in each test region may be determined according to the known or expected maximums and minimum constituent concentration in the aqueous fluid. By so doing, it is assured that the constituent concentration will not be less than or exceed the range of values detectable by the solid state test device.

The essential features of the solid state test device in accordance with the method of this invention are an inert support, a plurality of individual test regions spatially arranged on the support with the test regions separated from each other, e.g. as shown in FIG. 2, and each test region comprising an inert matrix impregnated with a reagent and a color indicator and wherein the amount of reagent in each test region differs from test region to test region in a predetermined manner.

The solid state test device in accordance with the method of this invention employs an inert support for carrying the plurality of test regions. This inert support is a continuous solid member that may have a variety of forms or shapes, including for example a band or strip, a circle and various other geometric shapes. Various materials may be employed for making the support, the essential features of the support being that it is a continuous solid and is inert and preferably non-porous. Particulate supports are not included in this invention. Examples of materials which may be used for making the support include, but are not limited to glass, metal, ceramics and plastics. Plastics may include, but are not limited to, polyolefins (e.g. polyethylene and polypropylene), polystyrene, polyesters (e.g. Mylar), polyacrylates, polyamides (e.g. nylon) polyvinyl chloride and polycarbonates. Preferably the support is made from inert, non-porous plastic because of the ease of handling, ease of making various support shapes, variety of plastics available, durability and low cost. Typically in the method of this invention the solid state test device employs an opaque or translucent support.

In accordance with the method of this invention the required solid state test device has a plurality of individual spaced apart test regions on the inert support. These test regions are porous in nature and may take on a variety of shapes or forms. One such form could be a pad having a square, rectangular, circular or other suitable geometric shape. The geometric shape of the test region is not a limiting factor in the method of this invention. Test regions may be housed on or within the support of the solid state test device in accordance with the method of this invention. Where the test region would be housed on the inert support the test region could be attached to the support by adhesive, mechanical or other suitable means.

The test region in accordance with this invention comprises an inert matrix impregnated with a color indicator and reagent interactive with the constituent whose concentration is being measured. Various matrix materials may be employed in the practice of this invention it being required that the matrix be inert and absorbent. Such matrix may be a woven or non-woven material and may include, but is not limited to, paper (e.g. filter paper), glass wool, polypropylene fiber mat, porous ceramic porous plastic, clathrate compounds and zeolites. The inert matrix is a material of sufficient porosity such as to take up and hold the reagent and the color indicator. In some practices of this invention the matrix may be in the form or structure of a sheet or film while in other practices of this invention the matrix may have a particulate form or structure. Preferably the matrix should have little or no color.

Various techniques may by employed to make the solid state test device in accordance with the method of this invention. For example, pieces of inert matrix (e.g. filter paper) could be impregnated with various amounts of reagent (e.g. impregnated with aqueous solutions of a water soluble solid organic acid having different concentrations of organic acid and a color indicator) and the pieces of impregnated inert matrix dried to retain the reagent therein. The dried pieces of reagent and color indicator impregnated matrix could then be cut into pads (i.e. test regions) and these pads adhered to an inert support, such as for example a strip of plastic film with the pads arranged along the strip of plastic film in an order of decreasing amount of reagent going from one end to the other end of the plastic film.

A test region having a known amount of reagent may be produced by: immersing a matrix strip of known size and weight in a solution (e.g. aqueous solution) of the reagent (i.e. known concentration of reagent) for a fixed time; allowing the immersed matrix strip to drain; and, drying (i.e. removing the solvent from the matrix), preferably to minimum constant weight. The dried reagent impregnated matrix strip would then be weighed and cut into uniform test regions of known size. The amount of reagent in a test region so prepared can be determined by simple division from the known size of the test region and known weight of the reagent impregnated into the matrix strip. This procedure could be used to produce successive test regions varying in the amount of reagent therein and thereby create the plurality of test regions of the solid state test device of the method of this invention.

The reagent impregnated into the matrix of the test region is a material interactive with the constituent whose concentration in the aqueous fluid composition is being measured. A variety of interactions between the reagent and the constituent may be employed in the practice of the method of this invention. Such interactions may include, but are not limited to, chemical reactions, complex formation and exchange interactions. Thus a wide variety of reagents may be employed in the practice of this invention. These reagents may include, but are not limited to, acids, bases, organic halides, sulfides, sulfonates, nitrates etc., clathrate compounds, chelating agents and ion exchange agents. The acids may be organic (e.g. citric, succinic, benzenesulfonic, oxalic, maleic, fumaric, oleic, phthalic and acetic) acids. Bases may include inorganic bases (e.g. sodium hydroxide, sodium carbonate, potassium hydroxide, calcium hydroxide) and basic organic compounds such as amines (e.g. $C_6$ to $C_{36}$ aliphatic mono and diamines, polyoxyalkylene mono and poly amines, fatty amines) and amides. The reagent may be an organic alcohol or polyol such as for example $C^6$–$C^{36}$ aliphatic mono alcohols, fatty alcohols, aliphatic polyols (e.g. diols) aromatic alcohols (e.g. phenol) and polyoxyalkylene polyols (e.g. diols). In providing stable and reliable test regions it is important for the reagent to be chemically stable in air and to have little or no volatility under normal (e.g. room temperature) ambient conditions. Thus the reagents suitable for use in the practice of this invention are those that are chemically stable in air and have very low or no volatility at room temperature conditions. Reagents suitable for use in this invention will be liquid or solid at room temperature (e.g. 20° to 40° C.). Liquid reagents must be absorbable into the matrix and resist desorbing or draining from the matrix. Solid reagents may be employed in solutions (e.g. aqueous, alcohol or aqueous/alcohol) form for impregnation into the matrix. Solid reagents are preferred.

It is particularly advantageous that the interaction between the reagent and fluid constituent for which concentration is to be determined be such that relatively small changes in the relative proportions of the reagent and constituent produce relative large changes in a condition detected by the color indicator. Thus, for example, where total alkalinity of the aqueous fluid is to be detected, it is desirable that a titration curve associated with reaction between the alkaline components of the aqueous fluid and an acid reagent to be impregnated in the test regions have a steep slope, i.e. relatively small changes in the proportions of the alkaline constituents and the acid reagent produce relatively large changes in pH within the test region. For use in determining concentration of metalworking fluids, total alkalinity of the fluid is determined preferably using organic acids having low pKa.

A color indicator is incorporated in the test region of the solid state test device in accordance with this invention. The color indicator is a substance that undergoes a change in color in response to interaction between the reagent in the test region and the constituent of the aqueous fluid composition whose concentration is being measured. The change in color may be from one color to another color (e.g. from red to blue, blue to white), from a color to no color, or from no color to a color. The color indicator preferably undergoes a change which is visually unambiguous in response to a change brought about by the interaction of the constituent and reagent. In one embodiment of this invention the color indicator will change color in response to an excess of the constituent in the test region over the amount of that constituent needed to interact with all of the reagent in the test region. In another embodiment of this invention the color indicator may exhibit a specific color in the presence of excess reagent over the amount needed to interact with the constituent and some other color or no color when there is no excess of the reagent in the test region. The change in color of the color indicator in accordance with this invention is preferably such as can readily be detected without resort to instrumentation.

A wide variety of color indicators may be used in the practice of this invention. The choice of color indicator can depend upon such factors as the composition of the reagent, the composition of the constituent, the composition and properties of the aqueous fluid composition, and the type of interaction between the reagent and the constituent. Color indicators are to be chosen that are specific to the interaction between the reagent and the constituent whose concentration is being measured. Color indicators usable in the practice of this invention may include, but are not limited to methyl orange, bromophenol blue, 4,4'-bis (2 amino-1-naphthylazo-2,2'-stilbenzdisulfonic acid, 2-(2,4-dinitrophenylazo)-1-naphthol-3, 6-disulfonic acid disodium salt, phenolphthalein, nitrazine yellow, bromocresol green, phenolsulfonephthalein, thymolsulfonephthalein and resorcin blue.

It is particularly advantageous if the color indicator undergoes a change in color over a narrow band of values of the condition of the test region to which the color indicator is color sensitive and the interaction between the reagent and aqueous fluid constituent produces a high ratio of change of that condition to changes of relative proportions of the reagent and constituent. In combination, a color indicator and constituent/reagent interaction so chosen can produce readily visually discriminated colors indicative of a condition of the fluid. For example, a reagent is chosen to interact with a constituent to change the pH of the aqueous fluid in such a way that relatively small changes in proportions of reagent and constituent produce relatively large changes of pH and, a pH color indicator is chosen which transitions over its entire range of colors over a narrow range of values of pH, for example, 1–1.5. Combining such a reagent with such a color indicator permits relatively small changes in proportions of reagent and constituent to cause changes of pH as great as or greater than the range of color transition of the pH color indicator. By providing plural test regions impregnated with differing amounts of such reagent and such color indicator, the test regions define discrete steps of concentration of constituent which are effective to produce color extremes of the pH color indicator. That is, differences in quantities of reagent from one test region to another are chosen so that a progression in discrete steps of concentration from one test region to another, at a predetermined resolution of concentration, is defined. Patterns of alternative colors produced by the pH color indicator among the plural test regions characterize concentration of the constituent with the resolution of such discrete steps.

In accordance with this invention, change in color in the test regions is the direct result of the contact of the test region with the aqueous fluid. In one practice of the method of this invention the change in color could result from the interaction of the color indicator with the constituent, the change in color occurring under the condition that the amount of constituent present in the test region exceeds the amount required to tie up, complex or otherwise consume, through reaction or interaction, all of the reagent in the test region. Thus where C represents the amount of constituent in a test region, R represents the amount of reagent in the test region and X represents the color indicator in the test region then the following two equations represent possible conditions in a test region after interaction or reaction with aqueous fluid constituent:

 (1)

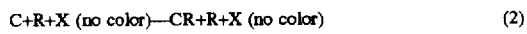 (2)

In equation 1, the amount of constituent C in the test region exceeds the amount needed to interact with all of reagent R present in the test region and forms CR. The excess constituent interacts with color indicator X to form CX, giving rise to a change in color of indicator X. In equation 2 the amount of constituent C in the test region is not sufficient to interact with all of the reagent R in the test region, leaving excess reagent R and indicator X which has not interacted with constituent C, hence no change in color occurs. The color change that occurs may be essentially from no color to a color, from a color to essentially no color or from one color to another color, including a change of from white to some other color (e.g. black, blue or red). The change will depend upon the color indicator being used. It is of course contemplated that an amount of color indicator would be employed in the test region to produce a visible change in color. There is also contemplated that the reagent and the color indicator could interact to produce a color and that the change in color of the test region may result from the interaction between all of the reagent in the test region with the constituent.

Determination of Concentration

There is provided in this invention a method of measuring the concentration of a constituent of an aqueous fluid composition. Although the method of this invention is specific to aqueous fluid compositions it is not limited by the constituents therein, it being required only that the constituent whose concentration is being measured be interactive with the reagent of the test region of the solid state test device and that the interaction between the constituent and the reagent lead to a change in color of the color indicator in the test region. Thus various aqueous fluid compositions may be employed in the embodiments of the method of this invention. These aqueous fluid compositions contain at least one constituent in addition to water and many of the aqueous fluids will contain several constituents in addition to water. Thus the aqueous fluid composition may be a complex mixture of a large number of constituents. Such aqueous fluids are often known or identified by their function, use or source and can thereby indicate to those skilled in the art the types of constituents therein. For example cooling water for a cold water air conditioning system or cooling tower can contain corrosion inhibitors, biocides, fungicides and algaecides. Aqueous fluid compositions usable in the embodiments of this invention include, but are not limited to, industrial aqueous fluids such as for example metal plating baths, aqueous based hydraulic fluids, cooling tower water, aqueous washing fluids and aqueous based machining fluids.

There is required in accordance with the method of this invention a step of contacting the solid state test device, described and defined herein, with an aqueous fluid composition. This contacting step may be accomplished by various techniques such as for example including, but not limited to, immersing the test device in the aqueous fluid, placing drops of the aqueous fluid onto the test device, wicking the aqueous fluid into the test device, pouring the aqueous fluid into the test device and coating the aqueous fluid onto the test device. The step of contacting the solid state test device should be accomplished in a manner that ensures uniform and complete contact of all the test regions of the solid state test device with the aqueous fluid. Such uniform and complete contact is preferred for properly carrying out the method of this invention and obtaining reliable test results. Persons skilled in the art will contemplate various other techniques for carrying out the contacting step of the method of this invention without departing from the spirit, intent and scope of this invention.

There is required in accordance with the method of this invention a step of comparing a constituent concentration color calibration scale to the solid state test device after contact of the device with the aqueous fluid. The constituent concentration color calibration scale may be made of or derived from a scale specific to the reagent, the constituent and the color indicator, i.e. a scale made from the same matrix, the same reagent and the same color indicator, used in the same amounts as used in the test regions of the solid state test device. The constituent concentration color calibration scale may be made of or derived from a series of the solid state test devices for which calibration is required. For example, a series of such solid state test devices may be exposed to a series of aqueous fluids having in known concentration the constituent of interest. These exposed solid state test devices may be arranged side by side and labeled in accordance with the known concentration of the constituent from the series of aqueous fluids.

For clarity the aqueous fluid composition used for contacting the solid state test device for measuring the constituent concentration shall be referred to herein as the test aqueous fluid composition and the aqueous fluid composition used for making the constituent concentration color calibration scale shall be called the calibration aqueous fluid composition. The test and calibration aqueous fluid compositions differ only in that the concentration of the test constituent is known in the calibration aqueous fluid composition and unknown in the test aqueous fluid composition. It is recognized that: a) the calibration aqueous fluid composition can comprise water and a known concentration of the aqueous fluid constituent the concentration of which is to be measured and; b) the constituent concentration color calibration scale can be prepared using calibration aqueous fluid compositions comprising water and known concentrations of the aqueous fluid constituent the concentration of which is to be measured.

In producing a constituent concentration color calibration scale, each of a series of solid state test devices is contacted by a calibration aqueous fluid composition having a different and known concentration of the test constituent. This produces a series of solid state test devices in which the color indicator of the various test regions have undergone a change in color in accordance with the concentration of the calibration aqueous fluids. Differences in amount of reagent in the test regions preferably progress uniformly along the length of the test device such that all test regions in which a change in color occurs are adjacent one to another, that is, such regions are not separated by regions in which no change in color occurs. Under these circumstances, a pattern of change of color is defined which may be represented by a legend comprising an index changing progressively from region to region along the length of the test strip.

Figure 4A:
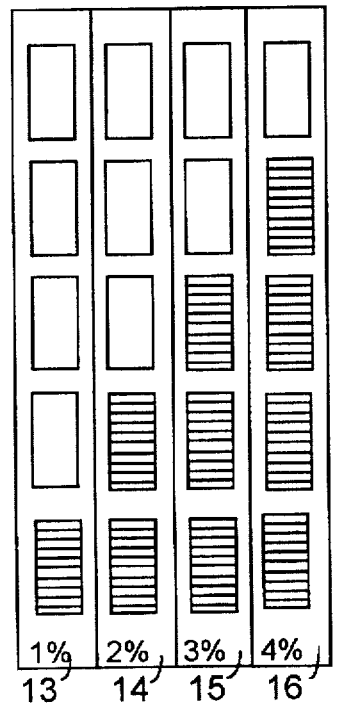
FIG. 4a is a constituent concentration color calibration scale.

In FIG. 4a is shown a constituent concentration color calibration scale 12 having four columns 13, 14, 15 and 16. Each column may be made of or derived from a solid state test device similar to that described with reference to FIG. 1 but including an additional test region. The columns 13, 14, 15 and 16 would therefore be specific to the reagent, the constituent and the color indicator, i.e. have or be derived from the same reagent and the same color indicator as solid state test device 1, would have the same predetermined variation of the amount of reagent from test region 3 to test region 6 with the exception of an additional test region having an amount of reagent differing from (e.g. more than) test region 6, and would be prepared from calibration aqueous fluids having known concentrations of the constituent(s) of interest. The matrix and support materials used for establishing the concentration color calibration scale must affect color produced by the color indicator in the presence of the reagent and aqueous fluid constituent in the same way in the concentration color calibration scale as in the test device.

Figure 4B:
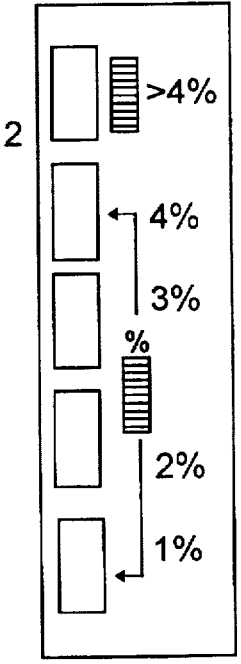

To establish a concentration color calibration scale, each of a series of solid state test devices is contacted by an aqueous fluid composition having a known and different concentration of the same constituent whose concentration is to be determined. Hence the pattern of test regions in which the color indicator has undergone a color change is established for known constituent concentrations over a range of concentrations. It is contemplated that having once established the pattern of color in the test regions for known concentrations, the concentration color calibration scale may be graphically reproduced or represented. Both colored and monochromatic representations may be employed, and a simple numerical scale may be developed indicating concentrations associated with the test regions so as to constitute the equivalent of the color calibration scale derived as described herein. The numerical scale equivalent of the color calibration scale may recite a series of concentration values (e.g. 1%, 2%, 3% etc.) or a series of numbers equivalent to concentration values as described. Such a numerical scale may be included as a legend on each solid state test device of the method of this invention as illustrated in FIG. 4b or may be provided on a separate chart.

In the method of this invention the solid state test device which is contacted with the test aqueous fluid composition, is visually compared to a constituent concentration color calibration scale. For example comparing the solid state test device 7 of FIG. 3 to the corresponding constituent concentration color calibration scale 12 of FIG. 4a there can be seen a pattern of changes of color of test regions (test regions 8, 9, and 10 having a different color than test region 11) which corresponds to the pattern of changes of color of column 15 of color calibration scale 12. As column 15 of color calibration scale 12 corresponds to a constituent concentration of 3%, it is known from test strip 7 of FIG. 3 that the constituent concentration of the test fluid is 3%.

Concentration of Aqueous Machining Fluids

In a preferred practice of the method of this invention there is employed as the aqueous fluid composition an aqueous based machining fluid composition. Aqueous based machining fluid compositions are employed in the shaping of solid workpieces, such as for example pieces of metal, into useful articles. In this shaping process or operation a cutting or non-cutting tool is applied against a workpiece to mechanically shape the article. This tool and/or the workpiece may be rotated with respect to each other, often at high speeds. Such high speeds are typically found in turning and grinding operations for shaping metals and other solid materials. In other cases the tool and workpiece are caused to have sliding contact with each other such as in a punching operation. Still other shaping operations cause a tool to be applied against the workpiece with great force without cutting the workpiece, such as in a metal rolling, drawing and ironing processes. High heat and friction are generated during these and other shaping methods causing such problems as tool wear, distortion of the finished article, poor surface finish and out of tolerance dimensions for the article. High scrap rates, tool wear and increased costs result from these problems. To overcome these and other problems it is known in the art to apply an aqueous machining fluid to the interface between a tool and the workpiece.

Aqueous based machining fluids are complex combinations of water, lubricant and additives such as for example surfactants, extreme pressure agents, corrosion inhibitors, bactericides and fungicides. The chemical condition of the aqueous based machining fluid is reflected by the concentrations of these constituents, each of which may perform one or more specific functions of the fluid. The lubricants and many other components of the aqueous based machining fluid are synthetic or naturally occurring organic compounds or mixtures of compounds. Lubricants useful in the aqueous based machining fluid may include for example esters, amides, polyethers, amines and sulfonated oils. The lubricant component reduces friction between the tool and workpiece while the water helps dissipate the heat generated in the metalworking operation. Corrosion inhibitors are employed to reduce or prevent corrosion of the workpiece and finished article as well as to reduce or prevent chemical attack on the tool. Bactericides and fungicides are used to reduce or prevent microbial or fungal attack on the constituents of the liquid, while the surfactant may be employed to form a stable suspension of water insoluble components in the water phase of the liquid. Thus each component has a function contributing to the overall utility and effectiveness of the machining fluid. The method of this invention for determination of concentration of constituents of an aqueous fluid is well suited to monitoring concentration of constituents of metalworking fluids, permitting timely, on site indications of constituent concentration.

A constituent concentration color calibration scale usable in the practice of the method of this invention for measuring the total alkalinity of an aqueous machining fluid may be prepared as follows. Individual strips of coarse filter paper nominally one fourth inch by two inches are immersed for a fixed time (e.g. 5 seconds) in 5 different ethanol impregnating solutions having the following compositions, drained, placed on a sheet of glass and dried in a 130° F. oven for 3 minutes to produce 5 impregnated strips having different amounts of maleic acid.

|                            | Impregnating Solution Composition |                                       |                  |
|----------------------------|-----------------------------------|---------------------------------------|------------------|
| Impregnating Solution No.  | 5% Maleic Acid Soln.* (gm.)       | 0.3% Bromophenol Blue Soln.** (gm.)   | Ethanol (gm.)    |
| 1                          | 2                                 | 1                                     | 17               |
| 2                          | 4.2                               | 1                                     | 14.8             |
| 3                          | 6.6                               | 1                                     | 12.4             |
| 4                          | 8.4                               | 1                                     | 10.6             |
| 5                          | 10                                | 1                                     | 9.0              |

*5% Maleic acid in ethanol
**0.3% Bromophenol blue in ethanol

Each of the impregnated and dried strips of filter paper is cut into 4 mm. wide bands producing bands numbered 1 to 5 corresponding to the 5 impregnating solutions. These five bands (i.e. bands numbered 1 to 5 corresponding to impregnating solutions numbered 1 to 5) each having a different amount of maleic acid therein, would be adhered to a sheet of polyvinyl chloride (PVC) film, arranged parallel to one another and spaced apart throughout their lengths and in an order of ascending maleic acid content. The PVC film having the five bands of impregnated filter paper adhered thereto is then cut in a direction transverse to the length of the bands into strips 4 to 5 mm. wide to produce calibration strips having 5 test pads or regions thereon used in conjunction with 2%, 4%, 6%, 8% and 10% dilutions of a freshly prepared calibrating aqueous machining fluid (i.e. 2%/98%, 4%/96%, 6%/94%, 8%/92% and 10%/90% fluid/water by weight). The test pads or regions of each of the calibration strips have a yellow color. The calibration strips are immersed in the calibration aqueous machining fluids, one calibration strip for each calibration fluid. The strips are allowed to drain for several seconds or shaken to remove excess fluid. Among the so exposed calibration strips, different numbers of test pads or regions exhibit changes of color from yellow to blue corresponding to the concentration of the alkaline constituents in the diluted calibrating aqueous machining fluid. By arranging the five immersed calibration strips side by side in order of increasing dilution of calibrating aqueous machining fluid in which each strip was immersed the following constituent concentration color calibration scale is presented for the alkaline constituents of the aqueous machining fluid.

| Aqueous machining fluid dilution | Number of yellow Pads | Number of Blue Pads |
|---|---|---|
| 0 | 5 | 0 |
| 2% | 4 | 1 |
| 4% | 3 | 2 |
| 6% | 2 | 3 |
| 8% | 1 | 4 |
| 10% | 0 | 5 |

Representative graphical depictions of color patterns may be derived from the above described constituent concentration color calibration scale. Hence, a graphical representation may be used as a constituent concentration color calibration scale as described, the representation depicting the patterns of changes of color of test regions appropriately labeled to associate concentration percentages with patterns of colors matching the patterns of colors of the exposed calibration strips as illustrated by FIG. 4a; or labels or a legend may be devised associating test regions along the length of a test strip with concentration percentages according to the progression of color change with concentration as determined by the calibration strips as illustrated by FIG. 4b.

In accordance with the method of this invention the constituent concentration color calibration scale as described is employed as follows: A solid state test device (i.e. test strip), prepared in the same manner as the calibration strips described above, is immersed for just long enough to wet the test strip, typically less than one second, in a test aqueous machining fluid having the same constituents as the calibration aqueous machining fluid. The test device is removed from the test fluid, shaken to remove excess test fluid and then compared to the constituent concentration color calibration scale. Concentration of alkaline constituents is evaluated from matching the pattern of colors in test regions of the test strip with the concentration color calibration scale. It will be appreciated that should all test regions of the test strip be blue, the concentration of alkaline constituents is known to be at least as great as 9%.

The total alkalinity (i.e. total alkaline content) of a used (i.e. test) aqueous machining fluid comprising water, mono and trialkanolamine, short chain mono and dicarboxylic acids, amine borate salts, triazoles and triazines is measured in accordance with the method of this invention by immersing a solid state test device, prepared in the same manner as the maleic acid bromophenol blue test strip described above, in the test aqueous machining fluid for several seconds, removing the test device from the fluid, shaking the test device to remove excess test fluid and comparing the immersed test device to a total alkalinity concentration color calibration scale. The total alkalinity concentration color calibration scale is prepared in the manner described herein using as the calibrating aqueous fluids, differing dilutions of the aforesaid aqueous machining fluid made from freshly prepared aqueous machining fluid.

In accordance with the method of this invention the total alkalinity (i.e. total alkaline content) of a used (i.e. test) aqueous machining fluid comprising water, mono and trialkanolamines, short chain mono and dicarboxylic acids, water soluble lubricants, triazoles and triazines is measured by immersing a solid state test device (i.e. test device), prepared in the same manner as the maleic acid bromophenol blue test strips described above, in the test aqueous machining fluid for several seconds, removing the test device from the test fluid, shaking the test device to remove excess test fluid and comparing the immersed test device to a total alkalinity concentration color calibration scale. The total alkalinity concentration color calibration scale is prepared in the manner described herein using as the calibrating aqueous fluids, differing dilutions of the aforesaid aqueous machining fluid, made from freshly prepared aqueous machining fluid.

The total alkalinity (i.e. total alkaline content) of a used aqueous machining fluid comprising water, mineral oil, anionic surfactants, alkanolamines, long chain fatty amides, triazoles and triazines is measured in accordance with the method of this invention by immersing a solid state test device (i.e. test device), prepared in the same manner as the maleic acid bromophenol blue test strip described above, in the test aqueous machining fluid for several seconds, removing the test device from the test fluid, shaking the test device to remove excess test fluid from the test device and comparing the immersed test device to a total alkalinity concentration color calibration scale. The total alkalinity concentration color calibration scale is prepared in the manner described herein using as the calibrating aqueous fluids, differing dilutions of the aforesaid aqueous machining fluid, made from freshly prepared aqueous machining fluid.

It is recognized that there has been discovered a solid state test device for measuring the concentration of a constituent of an aqueous fluid composition comprising an inert support and a plurality of individual spaced apart test regions spatially disposed on the support, wherein the test regions comprise an inert matrix impregnated with a reagent selectively interactive with the constituent whose concentration is being measured and a color indicator that produces a change in color in response to changes in the test region resulting from the direct contact of the test region with the aqueous fluid and the interaction between the reagent and the constituent whose concentration is being measured and wherein the amount of the reagent in each test region differs in a predetermined manner from the amount of reagent in adjacent test regions.

Further it is recognized that there has been discovered a test kit for measuring the concentration of a constituent of an aqueous fluid composition. The test kit comprises a) a solid state test device comprising an inert support and a plurality of individual spaced apart test regions spatially disposed on the support wherein the test regions comprise an inert matrix impregnated with a reagent selectively interactive with the constituent and a color indicator that produces a change in color in response to the changes in the test region resulting from the direct contact of the test region with the aqueous fluid composition and the interaction between the reagent and the constituent and wherein the amount of reagent in each test region differs in a predetermined manner from the amount of reagent in adjacent test regions and b) a constituent concentration color calibration scale prepared with the solid state test device and a plurality aqueous fluid compositions containing in known concentrations the constituent whose unknown concentration is being measured and wherein the constituent concentration color calibration scale comprises or is derived from a plurality of the solid state test devices which have been exposed to aqueous fluid compositions having known concentrations of the constituent whose unknown concentration is being measured.

While this invention and the practice thereof has been described with respect to various embodiments, it is recognized that one skilled in the art may practice further embodiments of the invention without departing from the spirit and scope of the invention set forth and claimed herein.

What is claimed is:

1. In a method of measuring the concentration of a constituent of an aqueous fluid composition the steps comprising a) contacting a solid state test device with the aqueous fluid composition, the solid state test device comprising an inert support and a plurality of individual spaced apart test regions on the support, wherein each test region comprises an inert matrix impregnated with a reagent selectively interactive with the constituent and a color indicator that produces a change in color in response to changes in the test region resulting from interaction between the reagent and the constituent and wherein the amount of the reagent in each test region differs in a predetermined manner from the amount of reagent in adjacent test regions, and b) comparing the solid state test device after contact with the aqueous fluid to a constituent concentration color calibration scale, whereby correspondence is determined between a pattern of resultant colors of the test regions and a constituent concentration represented by the constituent concentration color calibration scale.

2. The method of claim 1 wherein the constituent color calibration scale is specific to the reagent, the color indicator and the constituent.

3. The method of claim 1 wherein the constituent concentration is such that after contact with the aqueous fluid, a color change is produced in at least one but not all of the test regions.

4. The method of claim 1 wherein the reagent is a solid.

5. The method of claim 1 wherein the contacting of the solid state test device with the aqueous fluid composition is by immersing the solid state test device in the aqueous fluid composition.

6. The method of claim 1 wherein the reagent is also the color indicator.

7. The method of claim 1 wherein the interaction between reagent and constituent alters the pH in the test region and the color indicator is a pH color indicator.

8. The method of claim 7 wherein the reagent is chosen such that relatively large changes of pH are effected by relatively small changes in the proportions of reagent and constituent and the pH color indicator is chosen such that the band of pH over which its color changes is relatively narrow.

9. The method of claim 1 wherein the step of comparing the solid state test device after contact with the aqueous fluid composition to a constituent concentration color calibration scale is a step of visually comparing the solid state test device to a constituent concentration color calibration scale.

10. In a method of measuring the concentration of a constituent of an aqueous machining fluid composition, the steps comprising a) contacting a solid state test device with the aqueous machining fluid composition, the solid state test device comprising an inert support and a plurality of individual spaced apart test regions on the support, wherein each test region comprises an inert matrix impregnated with a reagent selectively interactive with the constituent and a color indicator that produces a color change in response to the changes in the test region resulting from interaction between the reagent and the constituent and wherein the amount of reagent in each test region differs in a predetermined manner from the amount of reagent in adjacent test regions and b) comparing the solid state test device after contact with the aqueous machining fluid to a constituent concentration color calibration scale, whereby correspondence is determined between a pattern of the resultant colors of the test regions and a constituent concentration represented by the constituent concentration color calibration scale.

11. The method of claim 10 wherein the interaction between reagent and constituent alters the pH in the test region and the color indicator is a pH color indicator.

12. The method of claim 11 wherein the reagent is chosen such that relatively large changes of pH are effected by relatively small changes in the proportions of reagent and constituent and the pH color indicator is chosen such that the band of pH over which its color changes is relatively narrow.

13. The method of claim 10 wherein the constituent concentration color calibration scale is specific to the reagent, the color indicator and the constituent.

14. The method of claim 10 wherein the constituent concentration is such that after contact with the aqueous machining fluid, a color change is produced in at least one but not all of the test regions.

15. The method of claim 10 wherein the step of comparing the solid state test device after contact with the aqueous machining fluid composition to a constituent concentration color calibration scale is a step of visually comparing the solid state test device to a constituent concentration color calibration scale.

16. In a method of measuring the total alkalinity of an aqueous machining fluid composition the steps comprising a) contacting a solid state test device with the aqueous machining fluid composition, the solid state test device comprising an inert support and a plurality of individual spaced apart test regions on the support, wherein each test region comprises an inert matrix impregnated with an acid reagent selectively interactive with the alkaline constituents of the aqueous machining fluid and an acid-base color indicator that produces a color change in response to the changes in the test region resulting from interaction between the acid reagent and the alkaline constituents of the aqueous machining fluid and wherein the amount of the acid reagent in each test region differs in a predetermined manner from the amount of acid reagent in adjacent test regions and b) comparing the solid state test device after contact with the aqueous machining fluid to a total alkalinity color calibration scale, whereby correspondence is determined between a pattern of the resultant colors of the test regions and a total alkalinity represented by the total alkalinity color calibration scale.

17. The method of claim 16 wherein the acid reagent is chosen such that relatively large changes of pH are effected by relatively small changes in the proportions of acid reagent and alkaline constituents of the aqueous machining fluid and the acid-base color indicator is chosen such that its color changes over a relatively narrow band of pH.

18. The method of claim 16 wherein the total alkalinity color calibration scale is specific to the acid reagent, the acid-base color indicator and the total alkalinity of the aqueous machining fluid composition.

19. The method of claim 16 wherein the total alkalinity of the aqueous machining fluid composition is such that after contact, a change in color is produced in at least one but not all of the test regions.

20. The method of claim 16 wherein the step of comparing the solid state test device after contact with the aqueous machining fluid composition to a total alkalinity constituent concentration color calibration scale is a step of visually comparing the solid state test device to a total alkalinity constituent concentration color calibration scale.

* * * * *